(12) United States Patent
Sampson et al.

(10) Patent No.: US 7,807,356 B2
(45) Date of Patent: Oct. 5, 2010

(54) LABELED NUCLEOTIDE COMPOSITION

(75) Inventors: Jeffrey R. Sampson, San Francisco, CA (US); Hui Wang, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 548 days.

(21) Appl. No.: 11/372,971

(22) Filed: Mar. 9, 2006

(65) Prior Publication Data

US 2007/0212697 A1    Sep. 13, 2007

(51) Int. Cl.
*C12Q 1/68* (2006.01)
(52) U.S. Cl. .......................................... 435/6

(58) Field of Classification Search ................. None
See application file for complete search history.

(56) References Cited

U.S. PATENT DOCUMENTS 7,019,129 B1 * 3/2006 Cook et al. ............... 536/26.6
2006/0115848 A1 * 6/2006 Blokhin et al. ................ 435/6

* cited by examiner

*Primary Examiner*—Gary Benzion
*Assistant Examiner*—Cynthia B Wilder

(57) ABSTRACT

Embodiments of labeled nucleotide compositions are described. Methods are described in which a sample containing RNA is contacted with an enzyme having an RNA ligation activity in the presence of a labeled nucleotide composition to provide labeled RNA. Methods of performing an array analysis of a labeled RNA sample are also described.

11 Claims, 5 Drawing Sheets

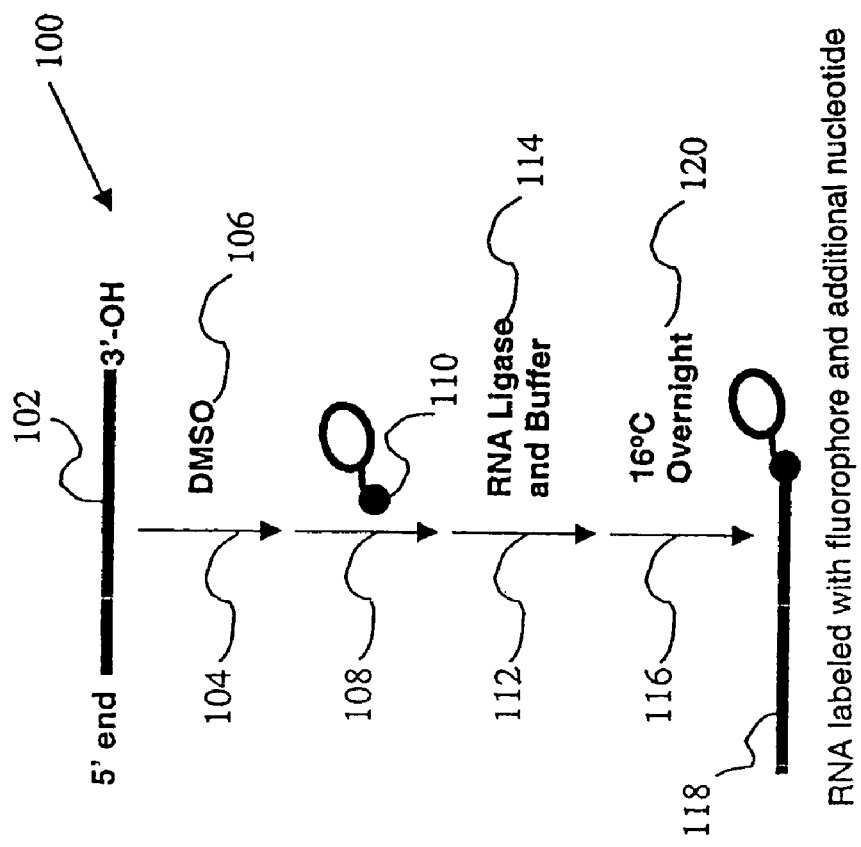
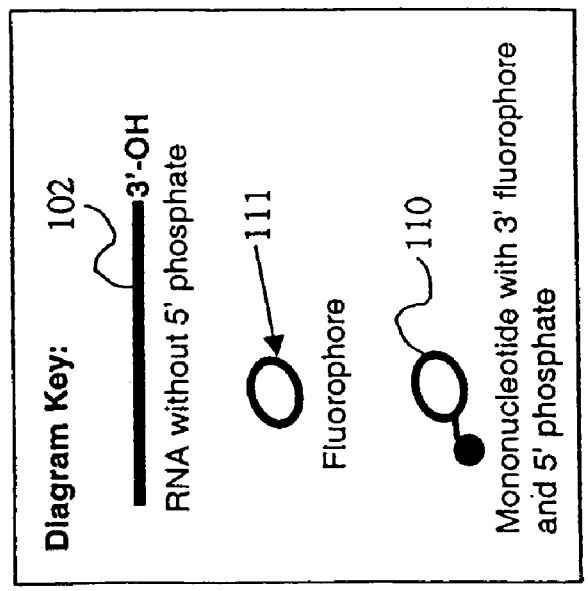
Fig._1

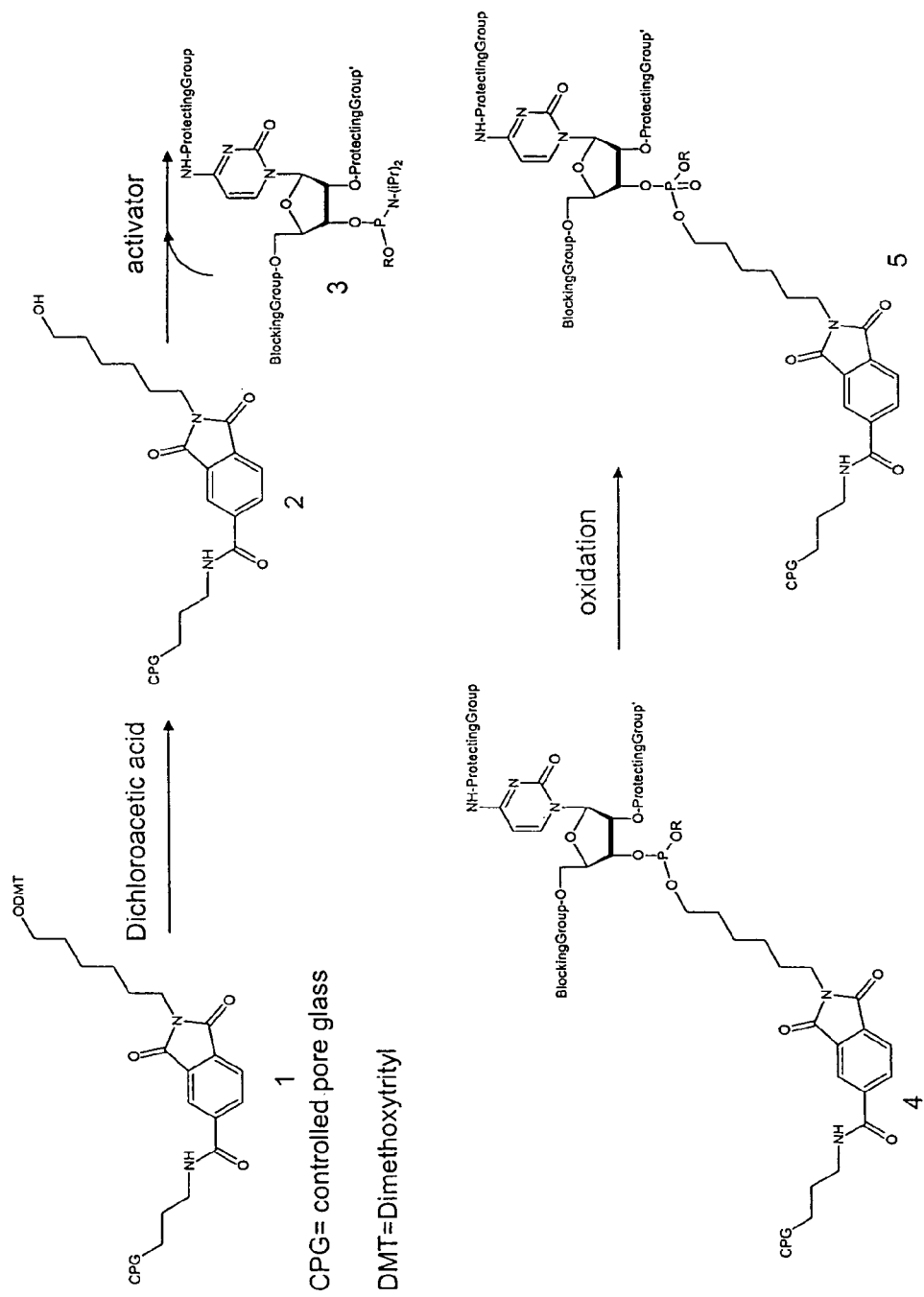
Fig._2

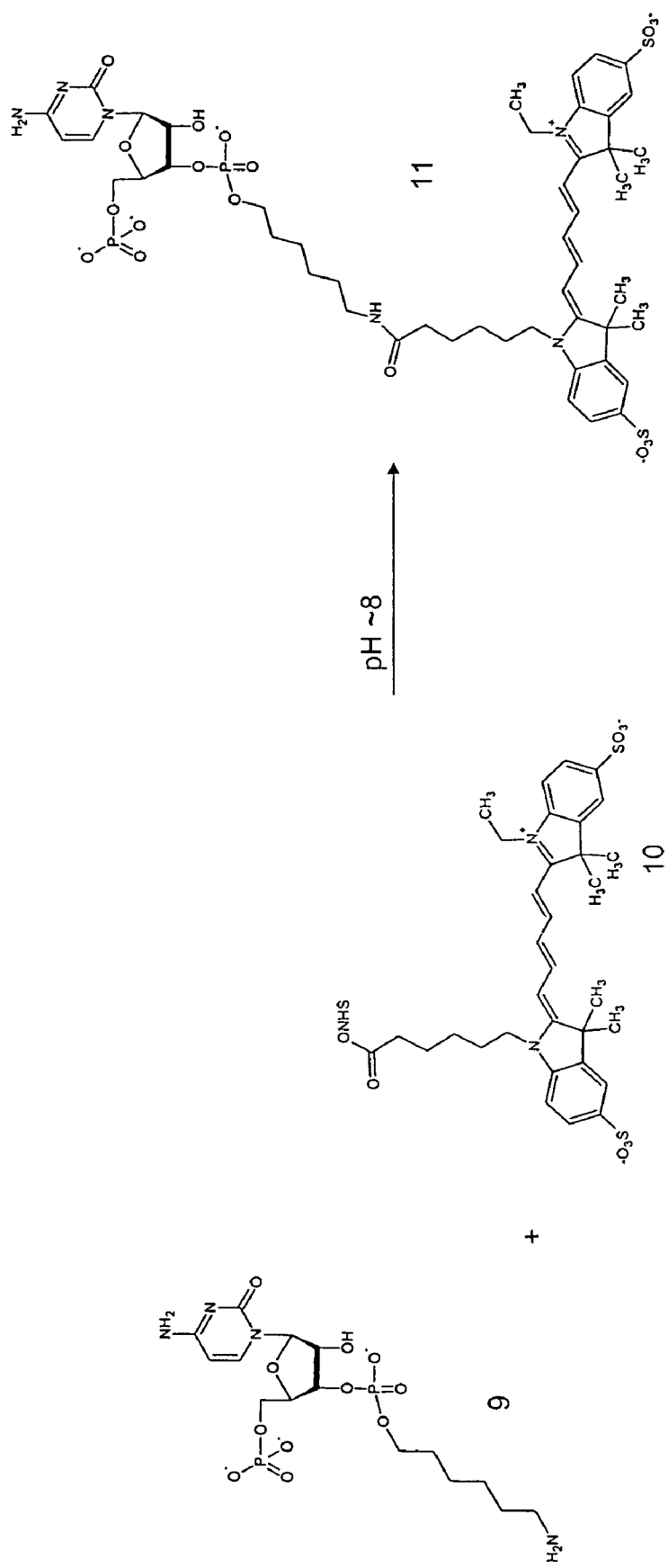
Fig. _ 4

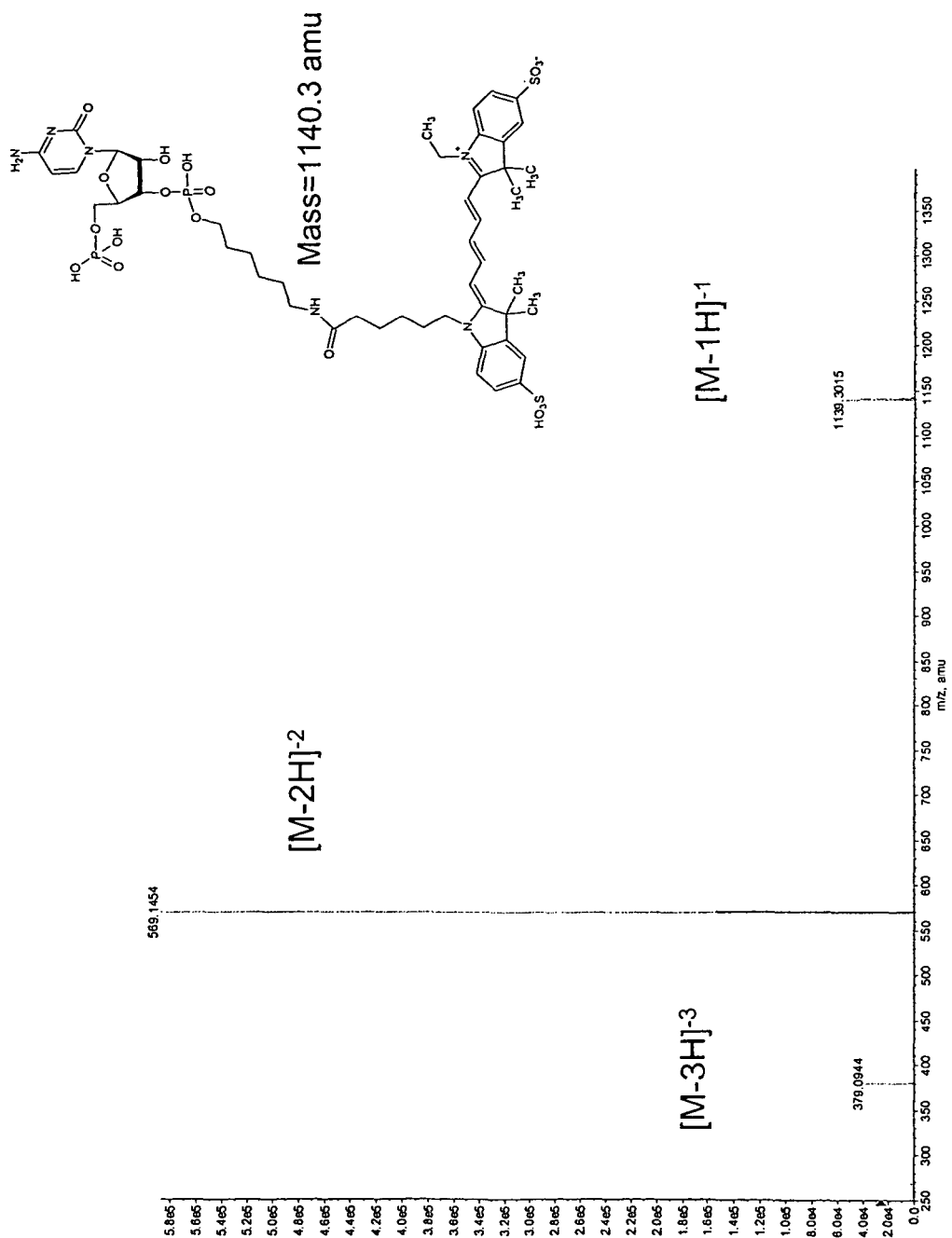
Fig._5

LABELED NUCLEOTIDE COMPOSITION

RELATED APPLICATIONS

Related subject matter is disclosed in U.S. patent application Ser. No. 11/048,225 filed on Jan. 31, 2005 by Wang.

DESCRIPTION

1. Field of the Invention

The invention relates generally to methods of biochemical analysis. More specifically, the invention relates to providing nucleotide compounds having an observable label and methods of use thereof.

2. Background of the Invention

Straightforward and reliable methods for simultaneously analyzing several constituents of a complex sample are extremely desirable. Polynucleotide arrays (such as DNA or RNA arrays) are known and are used, for example, as diagnostic or screening tools. Such arrays include regions of usually different sequence polynucleotides ("capture agents") arranged in a predetermined configuration on a support. The arrays are "addressable" in that these regions (sometimes referenced as "array features") have different predetermined locations ("addresses") on the support of array. The polynucleotide arrays typically are fabricated on planar supports either by depositing previously obtained polynucleotides onto the support in a site specific fashion or by site specific in situ synthesis of the polynucleotides upon the support. After depositing the polynucleotide capture agents onto the support, the support is typically processed (e.g., washed and blocked for example) and stored prior to use.

In use, an array is contacted with a sample or labeled sample containing analytes (typically, but not necessarily, other polynucleotides) under conditions that promote specific binding of the analytes in the sample to one or more of the capture agents present on the array. Thus, the arrays, when exposed to a sample, will undergo a binding reaction with the sample and exhibit an observed binding pattern. This binding pattern can be detected upon interrogating the array. For example all target polynucleotides (for example, DNA) in the sample can be labeled with a suitable label (such as a fluorescent compound), and the label then can be accurately observed (such as by observing the fluorescence pattern) on the array after exposure of the array to the sample. Assuming that the different sequence polynucleotides were correctly deposited in accordance with the predetermined configuration, then the observed binding pattern will be indicative of the presence and/or concentration of one or more components of the sample. Techniques for scanning arrays are described, for example, in U.S. Pat. Nos. 5,763,870 and 5,945,679. Still other techniques useful for observing an array are described in U.S. Pat. No. 5,721,435.

There has been great interest in the analysis of small RNAs, such as short interfering RNAs (siRNAs), microRNAs (miRNA), tiny non-codingRNAs (tncRNA) and small modulatory RNA (smRNA), since the discovery of siRNA biological activity over a decade ago. See Novina et al., Nature 430: 161-164 (2004). Even though the functions of most discovered miRNAs remain a mystery, it has become clear that they exist in abundance in plants and animals, with up to tens of thousands of copies per cell. In the fruit fly, at least 78 have been identified, and over 300 have been identified in human (see the public database accessible via the website accessed by typing "www" followed by ".sanger.ac.uk/cgi-bin/Rfam/ mirna/browse.pl" into the address bar of a typical internet browser). The levels of individual miRNAs seem to vary with developmental stages and tissue types. The level of fluctuation may be correlated with phenotype, mRNA levels, or protein levels for better biological insight. Thus quantitative measurements of miRNA may be of great importance. Further, viral miRNAs have been identified and may play a role in latency (see Pfeffer et al., Science, 304: 734-736 (2004)), making the detection and quantification of miRNAs a potentially valuable diagnostic tool.

Analytic methods employing polynucleotide arrays have been used for investigating these small RNAs, e.g. miRNAs have become a subject of investigation with microarray analysis. See, e.g., Liu et al., Proc. Nat'l Acad. Sci. USA, 101: 9740-9744 (2004); Thomson et al., Nature Methods, 1:1-7 (2004); and Babak et al., RNA, 10: 1813-1819 (2004). Methods of labeling RNAs are of interest for use in array analysis of RNA to provide an observable label used in interrogating the array. In the study of Liu et al., the miRNA was transcribed into DNA with a biotin-labeled primer. This primer was subsequently labeled with streptavidin-linked Alexa dye prior to array hybridization. This method is susceptible to any reverse-transcriptase reaction bias. Further, the streptavidin-dye as well as streptavidin-biotin-RNA stochiometry may be difficult to quantify. In the study of Thomson et al., the miRNA was directly labeled with 5'-phosphate-cytidyl-uridyl-Cy3-3' using T4 RNA ligase. This reaction is sensitive to the acceptor sequence. See England et al., Biochemistry, 17: 2069-2776 (1978). In the study of Babak et al (4), the miRNA was labeled with Ulysis Alexa Fluor system, which reacts with guanine residue (G) of RNA. Since different miRNAs do not have uniform G content, this method is not quantitative.

Thus, there is a continuing need for new compounds useful for labeling polynucleotides, and for methods of labeling RNA with such compounds. Such methods may be used in conjunction with analytical methods based on observing the label, such as array-based analysis of polynucleotides.

SUMMARY OF THE INVENTION

The invention thus relates to novel labeled nucleotide compositions. In particular embodiments, such labeled nucleotide compositions have the structure (I):

P1-Nus-P2-Lnk-Obs  (I)

wherein:
P1 is a phosphate group,
Nus is a nucleoside moiety comprising a sugar group bound to a purine or pyrimidine base;
P2 is a phosphate group;
Lnk is a linking group; and
Obs is an observable label moiety.

In particular embodiments, the labeled nucleotide compositions may be employed in methods for labeling RNA in a sample. In particular embodiments, the invention provides methods in which a sample containing RNA is contacted with an enzyme having an RNA ligation activity in the presence of the labeled nucleotide composition. This is done under conditions sufficient to result in coupling of the labeled nucleotide composition to the RNA in the sample to provide labeled RNA. In certain embodiments, the conditions sufficient to result in coupling include a DMSO concentration in the range from about 20% to about 30%.

Methods of performing an array analysis of an RNA sample are also taught herein. In certain embodiments, the invention provides a method of performing an array analysis wherein the method includes labeling the RNA in the sample to provide labeled RNA. The labeled RNA is then contacted with an array under conditions sufficient to provide for specific binding of labeled RNA to the array. The array typically is then interrogated to provide data on binding of RNA in the sample to the array.

Additional objects, advantages, and novel features of this invention shall be set forth in part in the descriptions and examples that follow and in part will become apparent to those skilled in the art upon examination of the following specifications or may be learned by the practice of the invention. The objects and advantages of the invention may be realized and attained by means of the instruments, combinations, compositions and methods particularly pointed out in the appended claims.

BRIEF DESCRIPTION OF THE DRAWINGS

These and other features of the invention will be understood from the description of representative embodiments of the method herein and the disclosure of illustrative apparatus for carrying out the method, taken together with the Figures, wherein FIG. 1 schematically illustrates embodiments of the present invention.

FIG. 2, FIG. 3, and FIG. 4 illustrate a synthesis of a labeled nucleotide composition in accordance with the present invention.

FIG. 5 is a mass spectrogram of a labeled nucleotide composition in accordance with the present invention.

To facilitate understanding, identical reference numerals have been used, where practical, to designate corresponding elements that are common to the Figures. Figure components are not drawn to scale.

DETAILED DESCRIPTION

Figure 3:
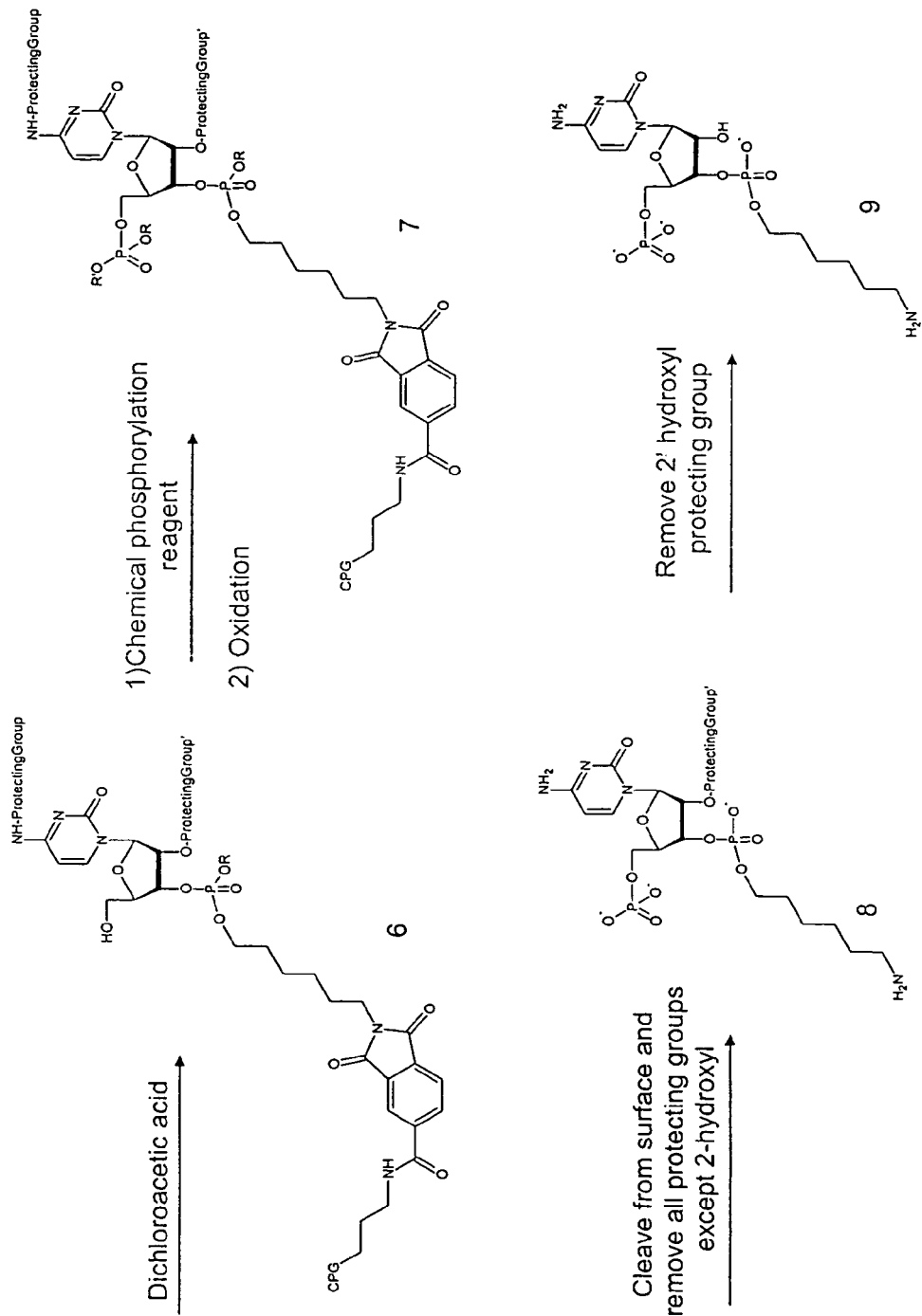

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

It must be noted that, as used in the specification and the appended claims, the singular forms "a," "an" and "the" include plural referents unless the context clearly dictates otherwise. Thus, for example, reference to "an insoluble support" includes a plurality of insoluble supports. Similarly, reference to "an RNA" includes a plurality of different identity (sequence) RNA species.

Furthermore, where a range of values is provided, it is understood that every intervening value, between the upper and lower limit of that range and any other stated or intervening value in that stated range is encompassed within the invention.

Also, it is contemplated that any optional feature of the inventive variations described may be set forth and claimed independently, or in combination with any one or more of the features described herein. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation. In this specification and in the claims that follow, reference will be made to a number of terms that shall be defined to have the following meanings unless a contrary intention is apparent.

"Optional" or "optionally" means that the subsequently described circumstance may or may not occur, so that the description includes instances where the circumstance occurs and instances where it does not. For example, if a step of a process is optional, it means that the step may or may not be performed, and, thus, the description includes embodiments wherein the step is performed and embodiments wherein the step is not performed (i.e. it is omitted).

An "oligonucleotide" is a molecule containing from 2 to about 100 nucleotide subunits. The term "nucleic acid" and "polynucleotide" are used interchangeably herein to describe a polymer of any length composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

A "nucleotide" refers to a sub-unit of a nucleic acid (whether DNA or RNA or analogue thereof) which includes a phosphate group, a sugar group and a nitrogen containing base, as well as analogs of such sub-units. A "nucleoside" references a nucleic acid subunit including a sugar group and a nitrogen containing base, as well as analogs of such subunits. One skilled in the art would have the understanding that additional modification to the nucleoside may be necessary and one skilled in the art has such knowledge. A "nucleoside moiety" refers to a molecule having a sugar group and a nitrogen containing base (as in a nucleoside) as a portion of a larger molecule, such as in a polynucleotide, oligonucleotide, or nucleoside phosphoramidite.

A "nucleotide monomer" refers to a molecule which is not incorporated in a larger oligo- or poly-nucleotide chain and which corresponds to a single nucleotide sub-unit; nucleotide monomers may also have activating or protecting groups, if such groups are necessary for the intended use of the nucleotide monomer.

The terms "nucleoside" and "nucleotide" are intended to include those moieties that contain not only the known purine and pyrimidine bases, e.g., but also other heterocyclic bases that have been modified. Such modifications include methylated purines or pyrimidines, acylated purines or pyrimidines, alkylated riboses or other heterocycles. Such modifications include, e.g., diaminopurine and its derivatives, inosine and its derivatives, alkylated purines or pyrimidines, acylated purines or pyrimidines thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, N,N-diphenyl carbamate, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural (not usually occurring in nature) nucleotides, unnatural nucleotide mimetics such as 2'-modified nucleosides, peptide nucleic acids, oligomeric nucleoside phosphonates, and any polynucleotide that has added substituent groups, such as protecting groups or linking groups.

By "protecting group" as used herein is meant a species which prevents a portion of a molecule from undergoing a specific chemical reaction, but which is removable from the molecule following completion of that reaction. A "hydroxyl protecting group" refers to a protecting group where the protected group is a hydroxyl.

"Moiety" and "group" are used to refer to a portion of a molecule, typically having a particular functional or structural feature, e.g. a linking group (a portion of a molecule connecting two other portions of the molecule), or an ethyl moiety (a portion of a molecule with a structure closely related to ethane). A moiety is generally bound to one or more other moieties to provide a molecular entity. As a simple example, a hydroxyl moiety bound to an ethyl moiety provides an ethanol molecule. At various points herein, the text may refer to a moiety by the name of the most closely related structure (e.g. an oligonucleotide moiety may be referenced as an oligonucleotide, a mononucleotide moiety may be referenced as a mononucleotide). However, despite this seeming informality of terminology, the appropriate meaning will be clear to those of ordinary skill in the art given the context, e.g. if the referenced term has a portion of its structure replaced with another group, then the referenced term is usually understood to be the moiety. For example, a mononucleotide moiety is a single nucleotide which has a portion of its structure (e.g. a hydrogen atom, hydroxyl group, or other group) replaced by a different moiety (e.g. a linking group, an observable label moiety, or other group). Similarly, an oligonucleotide moiety is an oligonucleotide which has a portion of its structure (e.g. a hydrogen atom, hydroxyl group, or other group) replaced by a different moiety (e.g. a linking group, an observable label moiety, or other group). "Nucleotide moiety" is generic to both mononucleotide moiety and oligonucleotide moiety.

The term "alkyl" as used herein, unless otherwise specified, refers to a saturated straight chain, branched or cyclic hydrocarbon group of 1 to 24, typically 1-12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

Moreover, the term "alkyl" includes "modified alkyl", which references an alkyl group having from one to twenty-four carbon atoms, and further having additional groups, such as one or more linkages selected from ether-, thio-, amino-, phospho-, oxo-, ester-, and amido-, and/or being substituted with one or more additional groups including lower alkyl, aryl, alkoxy, thioalkyl, hydroxyl, amino, sulfonyl, thio, mercapto, imino, halo, cyano, nitro, nitroso, azide, carboxy, sulfide, sulfone, sulfoxy, phosphoryl, silyl, silyloxy, and boronyl. Similarly, the term "lower alkyl" includes "modified lower alkyl", which references a group having from one to eight carbon atoms and further having additional groups, such as one or more linkages selected from ether-, thio-, amino-, phospho-, keto-, ester-, and amido-, and/or being substituted with one or more groups including lower alkyl; aryl, alkoxy, thioalkyl, hydroxyl, amino, sulfonyl, thio, mercapto, imino, halo, cyano, nitro, nitroso, azide, carboxy, sulfide, sulfone, sulfoxy, phosphoryl, silyl, silyloxy, and boronyl. The term "alkoxy" as used herein refers to a substituent —O—R wherein R is alkyl as defined above. The term "lower alkoxy" refers to such a group wherein R is lower alkyl. The term "thioalkyl" as used herein refers to a substituent —S—R wherein R is alkyl as defined above.

The term "alkenyl" as used herein, unless otherwise specified, refers to a branched, unbranched or cyclic (e.g. in the case of C5 and C6) hydrocarbon group of 2 to 24, typically 2 to 12, carbon atoms containing at least one double bond, such as ethenyl, vinyl, allyl, octenyl, decenyl, and the like. The term "lower alkenyl" intends an alkenyl group of two to eight carbon atoms, and specifically includes vinyl and allyl. The term "cycloalkenyl" refers to cyclic alkenyl groups.

The term "alkynyl" as used herein, unless otherwise specified, refers to a branched or unbranched hydrocarbon group of 2 to 24, typically 2 to 12, carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to eight carbon atoms, and includes, for example, acetylenyl and propynyl, and the term "cycloalkynyl" refers to cyclic alkynyl groups.

The term "aryl" as used herein refers to an aromatic species containing 1 to 5 aromatic rings, either fused or linked, and either unsubstituted or substituted with 1 or more substituents typically selected from the group consisting of lower alkyl, aryl, aralkyl, lower alkoxy, thioalkyl, hydroxyl, thio, mercapto, amino, imino, halo, cyano, nitro, nitroso, azide, carboxy, sulfide, sulfone, sulfoxy, phosphoryl, silyl, silyloxy, and boronyl; and lower alkyl substituted with one or more groups selected from lower alkyl, alkoxy, thioalkyl, hydroxyl thio, mercapto, amino, imino, halo, cyano, nitro, nitroso, azide, carboxy, sulfide, sulfone, sulfoxy, phosphoryl, silyl, silyloxy, and boronyl. Typical aryl groups contain 1 to 3 fused aromatic rings, and more typical aryl groups contain 1 aromatic ring or 2 fused aromatic rings. Aromatic groups herein may or may not be heterocyclic. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically aryl-substituted alkylene. Exemplary aralkyl groups have the structure —(CH2)j-Ar wherein j is an integer in the range of 1 to 24, more typically 1 to 6, and Ar is a monocyclic aryl moiety.

The term "halo" or "halogen" is used in its conventional sense to refer to a chloro, bromo, fluoro or iodo substituent.

"Linkage" as used herein refers to a first moiety bonded to two other moieties, wherein the two other moieties are linked via the first moiety. Typical linkages include ether (—O—), oxo (—C(O)—), amino (—NH—), amido (—N—C(O)—), thio (—S—), phospho (—P—), ester (—O—C(O)—).

"Functionalized" references a process whereby a material is modified to have a specific moiety bound to the material, e.g. a molecule or substrate is modified to have the specific moiety; the material (e.g. molecule or support) that has been so modified is referred to as a functionalized material (e.g. functionalized molecule or functionalized support).

The term "substituted" as used to describe chemical structures, groups, or moieties, refers to the structure, group, or moiety comprising one or more substituents. As used herein, in cases in which a first group is "substituted with" a second group, the second group is attached to the first group whereby a moiety of the first group (typically a hydrogen) is replaced by the second group.

"Substituent" references a group that replaces another group in a chemical structure. Typical substituents include nonhydrogen atoms (e.g. halogens), functional groups (such as, but not limited to amino, sulfhydryl, carbonyl, hydroxyl, alkoxy, carboxyl, silyl, silyloxy, phosphate and the like), hydrocarbyl groups, and hydrocarbyl groups substituted with one or more heteroatoms. Exemplary substituents include alkyl, lower alkyl, aryl, aralkyl, lower alkoxy, thioalkyl, hydroxyl, thio, mercapto, amino, imino, halo, cyano, nitro, nitroso, azide, carboxy, sulfide, sulfone, sulfoxy, phosphoryl, silyl, silyloxy, boronyl, and modified lower alkyl.

A "group" includes both substituted and unsubstituted forms. Typical substituents include one or more lower alkyl, modified alkyl, any halogen, hydroxy, or aryl. Any substituents are typically chosen so as not to substantially adversely affect reaction yield (for example, not lower it by more than 20% (or 10%, or 5% or 1%) of the yield otherwise obtained without a particular substituent or substituent combination).

Hyphens, or dashes, are used at various points throughout this specification to indicate attachment, e.g. where two named groups are immediately adjacent a dash in the text, this indicates the two named groups are attached to each other. Similarly, a series of named groups with dashes between each of the named groups in the text indicates the named groups are attached to each other in the order shown. Also, a single named group adjacent a dash in the text indicates the named group is typically attached to some other, unnamed group. In some embodiments, the attachment indicated by a dash may be, e.g. a covalent bond between the adjacent named groups. In some other embodiments, the dash may indicate indirect attachment, i.e. with intervening groups between the named groups. At various points throughout the specification a group may be set forth in the text with or without an adjacent dash, (e.g. amido or amido-, further e.g. alkyl or alkyl-, yet further e.g. Lnk, Lnk- or -Lnk-) where the context indicates the group is intended to be (or has the potential to be) bound to another group; in such cases, the identity of the group is denoted by the group name (whether or not there is an adjacent dash in the text). Note that where context indicates, a single group may be attached to more than one other group (e.g. where a linkage is intended, such as linking groups).

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present. At various points herein, a moiety may be described as being present zero or more times: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly. Similarly, a moiety may be described as being either (1) a group linking two adjacent groups, or (2) a bond linking the two adjacent groups: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly.

"Bound" may be used herein to indicate direct or indirect attachment. In the context of chemical structures, "bound" (or "bonded") may refer to the existence of a chemical bond directly joining two moieties or indirectly joining two moieties (e.g. via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect. "Free," as used in the context of a moiety that is free, indicates that the moiety is available to react with or be contacted by other components of the solution in which the moiety is a part.

The term "assessing" includes any form of measurement, and includes determining if an element is present or not. The terms "determining", "measuring", "evaluating", "assessing" and "assaying" are used interchangeably and may include quantitative and/or qualitative determinations. Assessing may be relative or absolute. "Assessing the presence of" includes determining the amount of something present and/or determining whether it is present or absent.

The term "mixture", as used herein, refers to a combination of elements, e.g., binding agents or analytes, that are interspersed and not in any particular order. A mixture is homogeneous and not spatially separated into its different constituents. Examples of mixtures of elements include a number of different elements that are dissolved in the same aqueous solution, or a number of different elements attached to a solid support at random or in no particular order in which the different elements are not spatially distinct. In other words, a mixture is not addressable. To be specific, an array of ligands, as is commonly known in the art, is not a mixture of ligands because the species of ligands are spatially distinct and the array is addressable.

"Isolated" or "purified" generally refers to isolation of a substance (compound, polynucleotide, protein, polypeptide, polypeptide, chromosome, etc.) such that the substance comprises a substantial portion of the sample in which it resides (excluding solvents), i.e. greater than the substance is typically found in its natural or un-isolated state. Typically, a substantial portion of the sample comprises at least about 5%, at least about 10%, at least about 20%, at least about 30%, at least about 50%, preferably at least about 80%, or more preferably at least about 90% of the sample (excluding solvents). For example, a sample of isolated RNA will typically comprise at least about 5% total RNA, where percent is calculated in this context as mass (e.g. in micrograms) of total RNA in the sample divided by mass (e.g. in micrograms) of the sum of (total RNA+other constituents in the sample (excluding solvent)). Techniques for purifying polynucleotides and polypeptides of interest are well known in the art and include, for example, gel electrophresis, ion-exchange chromatography, affinity chromatography, flow sorting, and sedimentation according to density. In typical embodiments, one or more of the sample, the enzyme having an RNA ligation activity, and the labeled nucleotide composition is in isolated form; more typically, all three are obtained in isolated form prior to use in the present methods.

The term "sample" as used herein relates to a material or mixture of materials, typically, although not necessarily, in fluid form, containing one or more components of interest.

The term "analyte" is used herein to refer to a known or unknown component of a sample. In certain embodiments of the invention, an analyte may specifically bind to a capture agent on a support surface if the analyte and the capture agent are members of a specific binding pair. In general, analytes are typically RNA or other polynucleotides. Typically, an "analyte" is referenced as a species in a mobile phase (e.g., fluid), to be detected by a "capture agent" which, in some embodiments, is bound to a support, or in other embodiments, is in solution. However, either of the "analyte" or "capture agent" may be the one which is to be evaluated by the other (thus, either one could be an unknown mixture of components of a sample, e.g., polynucleotides, to be evaluated by binding with the other). A "target" references an analyte.

The term "capture agent" refers to an agent that binds an analyte through an interaction that is sufficient to permit the agent to bind and concentrate the analyte from a homogeneous mixture of different analytes. The binding interaction may be mediated by an affinity region of the capture agent. Representative capture agents include polypeptides and polynucleotides, for example antibodies, peptides, or fragments of double stranded or single-stranded DNA or RNA may employed. Capture agents usually "specifically bind" one or more analytes.

The term "specific binding" refers to the ability of a capture agent to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold). In certain embodiments, the binding constant of a capture agent and analyte is greater than $10^6$ $M^{-1}$, greater than $10^7$ $M^{-1}$, greater than $10^8$ $M^{-1}$, greater than $10^9$ $M^{-1}$, greater than $10^{10}$ $M^{-1}$, usually up to about $10^{12}$ $M^{-1}$, or even up to about $10^{15}$ $M^{-1}$.

The term "stringent assay conditions" as used herein refers to conditions that are compatible to produce binding pairs of nucleic acids, e.g., capture agents and analytes, of sufficient complementarity to provide for the desired level of specificity in the assay while being incompatible to the formation of binding pairs between binding members of insufficient complementarity to provide for the desired specificity. Stringent assay conditions are the summation or combination (totality) of both hybridization and wash conditions.

A "stringent hybridization" and "stringent hybridization wash conditions" in the context of nucleic acid hybridization (e.g., as in array, Southern or Northern hybridizations) are sequence dependent, and are different under different experimental conditions. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO4, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions may affect the degree to which nucleic acids are specifically hybridized to complementary capture agents. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 1 to about 20 minutes; or, multiple washes with a solution with a salt concentration of about 0.1×SSC containing 0.1% SDS at 20 to 50° C. for 1 to 15 minutes; or, equivalent conditions. Stringent conditions for washing can also be, e.g., 0.2×SSC/0.1% SDS at 42° C. In instances wherein the nucleic acid molecules are deoxyoligonucleotides (i.e., oligonucleotides), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions.

A specific example of stringent assay conditions is rotating hybridization at a temperature of about 55° C. to about 70° C. in a salt based hybridization buffer with a total monovalent cation concentration of 1.5M (e.g., as described in U.S. patent application Ser. No. 09/655,482 filed on Sep. 5, 2000, the disclosure of which is herein incorporated by reference) followed by washes of 0.5×SSC and 0.1×SSC at room temperature and 37° C.

Stringent hybridization conditions may also include a "prehybridization" of aqueous phase nucleic acids with complexity-reducing nucleic acids to suppress repetitive sequences. For example, certain stringent hybridization conditions include, prior to any hybridization to surface-bound polynucleotides, hybridization with Cot-1 DNA or with random sequence synthetic oligonucleotides (e.g. 25-mers), or the like.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

The term "pre-determined" refers to an element whose identity is known prior to its use. For example, a "pre-determined analyte" is an analyte whose identity is known prior to any binding to a capture agent. An element may be known by name, sequence, molecular weight, its function, or any other attribute or identifier. In some embodiments, the term "analyte of interest", i.e., a known analyte that is of interest, is used synonymously with the term "pre-determined analyte".

The term "array" encompasses the term "microarray" and refers to an ordered array of capture agents for binding to aqueous analytes and the like. An "array" includes any two-dimensional or substantially two-dimensional (as well as a three-dimensional) arrangement of spatially addressable regions (i.e., "features") containing capture agents, particularly polynucleotides, and the like. Any given support may carry one, two, four or more arrays disposed on a surface of a support. Depending upon the use, any or all of the arrays may be the same or different from one another and each may contain multiple spots or features. A typical array may contain one or more, including more than two, more than ten, more than one hundred, more than one thousand, more ten thousand features, or even more than one hundred thousand features, in an area of less than 100 cm$^2$, 20 cm$^2$ or even less than 10 cm$^2$, e.g., less than about 5 cm$^2$, including less than about 1 cm$^2$, less than about 1 mm$^2$, e.g., 100 μm$^2$, or even smaller. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of the same or different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Arrays can be fabricated by depositing (e.g., by contact- or jet-based methods) either precursor units (such as nucleotide or amino acid monomers) or pre-synthesized capture agent. An array is "addressable" when it has multiple regions of different moieties (e.g., different capture agent) such that a region (i.e., a "feature" or "spot" of the array) at a particular predetermined location (i.e., an "address") on the array will detect a particular sequence. An "array layout" refers to one or more characteristics of the features, such as feature positioning on the support, one or more feature dimensions, and an indication of a moiety at a given location. "Interrogating" the array refers to obtaining information from the array, especially information about analytes binding to the array. "Hybridization assay" references a process of contacting an array with a mobile phase containing analyte. An "array support" refers to an article that supports an addressable collection of capture agents.

"Complementary" references a property of specific binding between polynucleotides based on the sequences of the polynucleotides. As used herein, polynucleotides are complementary if they bind to each other in a hybridization assay under stringent conditions, e.g. if they produce a given or detectable level of signal in a hybridization assay. Portions of polynucleotides are complementary to each other if they follow conventional base-pairing rules, e.g. A pairs with T (or U) and G pairs with C. "Complementary" includes embodiments in which there is an absolute sequence complementarity, and also embodiments in which there is a substantial sequence complementarity. "Absolute sequence complementarity" means that there is 100% sequence complementarity between a first polynucleotide and a second polynucleotide, i.e. there are no insertions, deletions, or substitutions in either of the first and second polynucleotides with respect to the other polynucleotide (over the complementary region). Put another way, every base of the complementary region may be paired with its complementary base, i.e. following normal base-pairing rules. "Substantial sequence complementarity" permits one or more relatively small (less than 10 bases, e.g. less than 5 bases, typically less than 3 bases, more typically a single base) insertions, deletions, or substitutions in the first and/or second polynucleotide (over the complementary region) relative to the other polynucleotide. The region that is complementary between a first polynucleotide and a second polynucleotide (e.g. a target analyte and a capture agent) is typically at least about 10 bases long, more typically at least about 15 bases long, still more typically at least about 20 bases long, or at least about 25 bases long. In various typical embodiments, the region that is complementary between a first polynucleotide and a second polynucleotide (e.g. target analyte and a capture agent) may be up to about 200 bases long, or up to about 120 bases long, up to about 100 bases long, up to about 80 bases long, up to about 60 bases long, or up to about 45 bases long.

"Upstream" as used herein refers to the 5' direction along a polynucleotide, e.g. an RNA molecule. "Downstream" refers to the 3' direction along the polynucleotide. Hence, a label downstream of an analyte is located at (or is bound to) a nucleotide moiety that is located in the 3' direction from the analyte, e.g. bound to the 3' end of the analyte. Similarly, an "upstream label" references a label that is located at (or is bound to) a nucleotide moiety that is located in the 5' direction from the analyte, e.g. bound to the 5' end of the analyte. "3'-" and "5'-" have their conventional meaning as known in the art.

Accordingly, in some embodiments of the present invention, a labeled nucleotide composition is provided. In particular embodiments, the labeled nucleotide composition has the structure (I):

P1-Nus-P2-Lnk-Obs     (I)

wherein:

P1 is a phosphate group,

Nus is a nucleoside moiety comprising a sugar group bound to a purine or pyrimidine base;

P2 is a phosphate group;

Lnk is a linking group; and

Obs is an observable label moiety.

In certain embodiments, a labeled nucleotide composition in accordance with the present invention is a salt, conjugate base, tautomer, or ionized form of a composition having structure (I).

In typical embodiments the phosphate group P1 is a phosphate group and may be represented as:

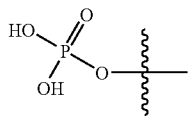

The broken line represents the bond at which the phosphate group P1 is attached to the nucleoside moiety Nus. As is well known, one or both of the hydroxyl groups of the phosphate group P1 may be ionized, depending on the environment of the phosphate group. Such ionized forms are hereby denoted to be included in the broader term "phosphate group" as used herein. Also, monobasic or dibasic phosphate salts, e.g. sodium biphosphate salt or disodium phosphate salt, are hereby denoted to be included in the broader term "phosphate group" as used herein.

In typical embodiments the phosphate group P2 is a phosphate group and may be represented as:

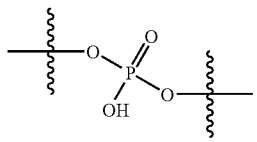

The first broken line represents the bond at which the phosphate group P2 is attached to the nucleoside moiety Nus. The second broken line represents the bond at which the phosphate group P2 is attached to the linking group Lnk. As is well known, the hydroxyl group of the phosphate group P2 may be ionized, depending on the environment of the phosphate group. Such ionized form is hereby denoted to be included in the broader term "phosphate group" as used herein. Also, corresponding monobasic phosphate salts, e.g. a sodium or potassium salt, are hereby denoted to be included in the broader term "phosphate group" as used herein.

Again referring to structure (I), in typical embodiments the nucleoside moiety Nus includes a sugar group bound to a purine or pyrimidine base. The sugar group of the nucleoside moiety may be any sugar group known in the art of polynucleotides and polynucleotide analogues. Representative sugar groups may be selected from monosaccharides, ketoses, aldoses, pentoses (five carbon sugars), hexoses (six carbon sugars), including any such groups modified by e.g. oxidation, deoxygenation, introduction of other substituents, alkylation and acylation of hydroxyl groups, and chain branching. The sugar group is typically ribose or 2'-deoxyribose, although other sugars may be used. In an embodiment, the sugar is arabinose. In another embodiment, the sugar is selected from xylose or lyxose. In typical embodiments, the sugar group is a monosaccharide; representative monosaccharides include glycerose, dihydroxyacetone, erythrose, erythrulose, xylose, lyxose, arabinose, ribose, xylulose, ribulose, rhamnose, fucose, glucose, mannose, galactose, fructose, sorbose, glucoheptose, galamannoheptose, sedoheptulose, mannoheptulose, and others.

In typical embodiments, the sugar group has a 5' site, a 3' site, and a 1' site. In typical embodiments, the sugar group is bound to the phosphate group P1 at the 5' site of the sugar group. Also in typical embodiments, the sugar group is bound to the phosphate group P2 at the 3' site of the sugar group. In typical embodiments, the phosphate group P1 is attached to the phosphate group P2 via the intermediate sugar group. And, typically the sugar group is bound to the purine or pyrimidine base at the 1' site of the sugar group. In certain embodiments, the sugar group includes a hydroxyl protecting group, e.g. at the 2' site of the sugar group. Examples of suitable hydroxyl protecting groups are described in "Protective Groups in Organic Synthesis" by T. W. Green, Wiley Interscience.

As mentioned with regard to structure (I), in typical embodiments the nucleoside moiety Nus includes a purine or pyrimidine base bound to the sugar group. In the case of a purine base, the purine base is typically attached to the sugar group at the $N^9$ position of the purine base. In the case of a pyrimidine base, the pyrimidine base is typically attached to the sugar group at the $N^1$ position of the pyrimidine base.

As described above with regard to structure (I), the Nus group is a nucleoside moiety having a sugar group bound to a purine or pyrimidine base. The purine or pyrimidine base of the nucleoside moiety may be selected from the naturally occurring purine and pyrimidine bases, e.g., adenine (A), thymine (T), cytosine (C), guanine (G), or uracil (U), or modified purine and pyrimidine bases, and common analogs, e.g. such as are recited herein. Certain purine or pyrimidine analogs that are contemplated in this context include those described in U.S. patent application Ser. No. 10/324,409 entitled "Method of Producing Nucleic Acid Molecules with Reduced Secondary Structure", filed on Dec. 18, 2002, and also those described in U.S. patent application Ser. No. 09/358,141 entitled "Method of Producing Nucleic Acid Molecules with Reduced Secondary Structure", filed on Jul. 20, 1999. In particular embodiments, the purine or pyrimidine base may have a protecting group, as is commonly known in the art of polynucleotide synthesis.

In certain embodiments, the purine or pyrimidine base is selected from 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

The purine or pyrimidine base is typically bound by an N-glycosidic linkage to the 1' site (i.e. the 1' carbon) of the sugar group, although other configurations are to be encompassed by the invention. In other embodiments, the purine or pyrimidine base is bound by a C-glycosidic linkage to the 1' site of the sugar group. In some embodiments the purine or pyrimidine base is bound at a site other than the 1' site of the sugar group. Other positions of the purine or pyrimidine base (the atom of the purine or pyrimidine base via which the purine or pyrimidine base is linked to the sugar group) and other linkages between the purine or pyrimidine base and the sugar group may be practiced by those of ordinary skill in the synthesis of nucleotide analogs given the disclosure herein, especially where analogous structures having the given purine or pyrimidine base and sugar group are known in the art.

Still referring to structure (I), the linking group Lnk is selected from (1) a linking group linking the phosphate group P2 and the observable label moiety Obs; or (2) a covalent bond between the phosphate group P2 and the observable label moiety Obs (e.g. the observable label moiety Obs is directly bound to an oxygen of the phosphate group P2). In particular embodiments, the linking group Lnk may be any appropriate linking group via which the phosphate group P2 is attached to the observable label moiety Obs. The linking group Lnk is typically selected from (1) a lower alkyl group; (2) a modified lower alkyl group in which one or more linkages selected from ether-, thio-, amino-, oxo-, ester-, and amido- is present; (3) a modified lower alkyl substituted with one or more groups including lower alkyl; aryl, aralkyl, alkoxyl, thioalkyl, hydroxyl, amino, sulfonyl, halo; or (4) a modified lower alkyl substituted with one or more groups including lower alkyl; alkoxyl, thioalkyl, hydroxyl, amino, sulfonyl, halo, and in which one or more linkages selected from ether-, thio-, amino-, oxo-, ester-, and amido- is present. The linking group Lnk may be bonded to the adjacent phosphate group P2 at any position of the linking group Lnk available to bind to the adjacent phosphate group P2. Similarly, the linking group Lnk may be bonded to the adjacent observable label moiety Obs at any position of the linking group Lnk available to bind to the adjacent observable label moiety Obs. In certain embodiments, the linking group Lnk is a single methylene group, e.g. —CH$_2$—, or may be an alkyl group or modified alkyl group up to about 24 carbons long (and which may be straight-chain or branched-chain). In certain such embodiments, one or more linkages selected from ether-, oxo-, thio-, and amino- is present in the straight- or branched chain modified alkyl group. In an embodiment, the linking group Lnk comprises optionally substituted ethoxy, propoxy, or butoxy groups (i.e. may include the structure —{(CH$_2$)$_m$—O}$_n$—, wherein m is a integer selected from 2, 3, 4, and n is a integer selected from 1, 2, 3, 4, 5, 6). In an embodiment, the linking group Lnk has the structure —(CH$_2$)$_m$-Lkg-(CH$_2$)$_n$—, wherein m and n are integers independently selected from the range of 1 to about 12, e.g. from the range of 2 to about 8, and Lkg is a linkage selected from ether-, thio-, amino-, oxo-, ester-, and amido-. In an example, Lnk has the structure —(CH$_2$)$_m$—NH—C(O)—(CH$_2$)$_n$—, wherein m and n are integers independently selected from the range of 1 to about 12, e.g. from the range of 2 to about 8, e.g. from the range of 3 to about 6; in a particular embodiment, m is 6 and n is 5.

In particular embodiments, the linking group Lnk has a first terminal site and a second terminal site. In such embodiments, the linking group Lnk is bound to the phosphate P2 at the first terminal site and the linking group Lnk is bound to the observable label moiety at the second terminal site. The first and second terminal sites will depend on the design of the linking group taking into consideration, for example, the method used to attach the observable label moiety to the rest of the labeled nucleotide composition.

In typical embodiments, a labeled nucleotide composition provided in accordance with the present invention has the structure (II)

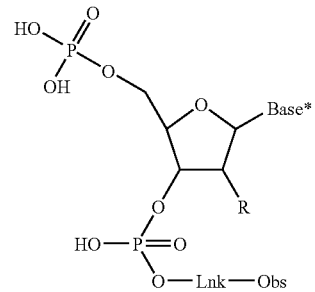

(II)

Wherein:
Base* is a purine or pyrimidine base;
R is H, OH, or a hydroxyl protecting group;
Lnk is a linking group; and
Obs is an observable label moiety.

As is well known, one or more hydroxyl groups of the phosphate groups may be ionized, depending on the environment of the phosphate groups. Compositions differing from the structure (II) only by the acid-base removal or addition of a hydrogen ion, such as occurs in aqueous solution at a pH in the range of about 4 to about 11, are referenced herein as "ionized forms" of structure (II), and should be considered essentially equivalent to the structure (II). Also, salts of the compositions of structure (II), e.g. monobasic or dibasic phosphate salts, e.g. sodium or potassium salts thereof, should be considered essentially equivalent to the structure (II). It should also be noted that the convention of not drawing individual hydrogens attached to the main carbon chain typically has been adhered to, and that such hydrogens would be understood to be present by one of skill in the art.

Referring to structure (II), Base* is a purine or pyrimidine base and in typical embodiments may be selected from the naturally occurring purine and pyrimidine bases, e.g., adenine (A), thymine (T), cytosine (C), guanine (G), or uracil (U), or modified purine and pyrimidine bases, and common analogs, e.g. such as are recited herein. Certain purine or pyrimidine analogs that are contemplated in this context include those described in U.S. patent application Ser. No. 10/324,409 entitled "Method of Producing Nucleic Acid Molecules with Reduced Secondary Structure", filed on Dec. 18, 2002, and also those described in U.S. patent application Ser. No. 09/358,141 entitled "Method of Producing Nucleic Acid Molecules with Reduced Secondary Structure", filed on Jul. 20, 1999. In particular embodiments, the purine or pyrimidine base may have a protecting group, as is commonly known in the art of polynucleotide synthesis.

In certain embodiments, the purine or pyrimidine base (Base*) is selected from 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

The purine or pyrimidine base (Base*) is typically bound by an N-glycosidic linkage to the 1' site (i.e. the 1' carbon) of the sugar group, although other configurations are to be encompassed by the invention. In other embodiments, the purine or pyrimidine base is bound by a C-glycosidic linkage to the 1' site of the sugar group. In some embodiments the purine or pyrimidine base is bound at a site other than the 1' site of the sugar group. In the case of a purine base, the purine base is typically attached to the sugar group at the $N^9$ position of the purine base. In the case of a pyrimidine base, the pyrimidine base is typically attached to the sugar group at the $N^1$ position of the pyrimidine base. Other positions of the purine or pyrimidine base (the atom of the purine or pyrimidine base via which the purine or pyrimidine base is linked to the sugar group) and other linkages between the purine or pyrimidine base and the sugar group may be practiced by those of ordinary skill in the synthesis of nucleotide analogs given the disclosure herein, especially where analogous structures having the given purine or pyrimidine base and sugar group are known in the art.

Still referring to structure (II), R is H, OH, or a hydroxyl protecting group. The hydroxyl protecting group may be any suitable known protecting group, and will be selected based on experimental design and intended use of the composition of structure (II). For example, the hydroxyl protecting group should be selected to be stable during experimental conditions at which the 2' site of the sugar group requires a protecting group. Furthermore, the hydroxyl protecting group should be selected to be labile under conditions that do not degrade the composition of structure (II) or interfere with the intended use of the composition of structure (II). Examples of suitable hydroxyl protecting groups are described in "Protective Groups in Organic Synthesis" by T. W. Green, Wiley Interscience.

Still referring to structure (II), the linking group Lnk is selected from (1) a linking group linking the phosphate group (i.e. the phosphate group at the 3' position of the sugar) and the observable label moiety Obs; or (2) a covalent bond between the phosphate group (i.e. the phosphate group at the 3' position of the sugar) and the observable label moiety Obs (e.g. the observable label moiety Obs is directly bound to an oxygen of the phosphate group). In particular embodiments, the linking group Lnk may be any appropriate linking group via which the phosphate group (i.e. the phosphate group at the 3' position of the sugar) is attached to the observable label moiety Obs. The linking group Lnk is typically selected from (1) a lower alkyl group; (2) a modified lower alkyl group in which one or more linkages selected from ether-, thio-, amino-, oxo-, ester-, and amido- is present; (3) a modified lower alkyl substituted with one or more groups including lower alkyl; aryl, aralkyl, alkoxyl, thioalkyl, hydroxyl, amino, sulfonyl, halo; or (4) a modified lower alkyl substituted with one or more groups including lower alkyl; alkoxyl, thioalkyl, hydroxyl, amino, sulfonyl, halo, and in which one or more linkages selected from ether-, thio-, amino-, oxo-, ester-, and amido- is present. The linking group Lnk may be bonded to the adjacent phosphate group (i.e. the phosphate group at the 3' position of the sugar) at any position of the linking group Lnk available to bind to the adjacent phosphate group. Similarly, the linking group Lnk may be bonded to the adjacent observable label moiety Obs at any position of the linking group Lnk available to bind to the adjacent observable label moiety Obs. In certain embodiments, the linking group Lnk is a single methylene group, e.g. —$CH_2$—, or may be an alkyl group or modified alkyl group up to about 24 carbons long (and which may be straight-chain or branched-chain). In certain such embodiments, one or more linkages selected from ether-, oxo-, thio-, and amino- is present in the straight- or branched chain modified alkyl group. In an embodiment, the linking group Lnk comprises optionally substituted ethoxy, propoxy, or butoxy groups (i.e. may include the structure —$\{(CH_2)_m—O\}_n$—, wherein m is a integer selected from 2, 3, 4, and n is a integer selected from 1, 2, 3, 4, 5, 6). In an embodiment, the linking group Lnk has the structure —$(CH_2)_m$-Lkg-$(CH_2)_n$—, wherein m and n are integers independently selected from the range of 1 to about 12, e.g. from the range of 2 to about 8, and Lkg is a linkage selected from ether-, thio-, amino-, oxo-, ester-, and amido-. In an example, Lnk has the structure —$(CH_2)_m$—NH—C(O)—$(CH_2)_n$—, wherein m and n are integers independently selected from the range of 1 to about 12, e.g. from the range of 2 to about 8, e.g. from the range of 3 to about 6; in a particular embodiment, m is 6 and n is 5.

In particular embodiments, the linking group Lnk has a first terminal site and a second terminal site. In such embodiments, the linking group Lnk is bound to the phosphate P2 at the first terminal site and the linking group Lnk is bound to the observable label moiety Obs at the second terminal site. The first and second terminal sites will depend on the design of the linking group taking into consideration, for example, the method used to attach the observable label moiety Obs to the rest of the labeled nucleotide composition.

The observable label moiety Obs is a moiety that provides for an observable signal that indicates the presence of the observable label moiety Obs. The signal is detectable by any suitable means, including spectroscopic, photochemical, biochemical, immunochemical, electrical, optical or chemical means. In typical embodiments, the observable label moiety Obs may be a chromogenic moiety, a fluorophore, a mass label, a spin label, a radiolabel, or other labels known in the art.

In particular embodiments, the observable label moiety Obs is a fluorophore selected from the group consisting of Cy3, Cy5, and an Alexa dye. Further examples of observable label moieties include any commercially available fluorophores that can be conjugated to mononucleotides or polynucleotides, e.g. dyes from Molecular Probes (Eugene, Oreg. and Leiden, The Netherlands) such as the Alexa Fluor series (example: Alexa 350, Alexa 430, Alexa 532, Alexa 546, Alexa 568, and Alexa 594) and the series of BODIPY conjugates. Other examples include: Tamra, Fluorescein, carboxyfluorescein, JOE, rhodamine, carboxyrhodamine, CY series, Oyster series. A number of fluorescent compounds are suitable to employ as the observable label moiety Obs in the present invention. Nonlimiting examples of such fluorescent compounds include the following: dansyl chloride; fluoresceins, such as 3,6-dihydroxy-9-phenylxanthhydrol; rhodamineisothiocyanate; N-phenyl-1-amino-8-sulfonatonaphthalene; N-phenyl-2-amino-6-sulfonatonaphthanlene; 4-acetamido-4-isothiocyanatostilbene-2,2'-disulfonic acid; pyrene-3-sulfonic acid; 2-toluidinonapththalene-6-sulfonate; N-phenyl, N-methyl 2-aminonaphthalene-6-sulfonate; ethidium bromide; stebrine; auromine-0,2-(9'-anthroyl)palmitate; dansyl phosphatidylethanolamin; N,N'-dioctadecyl oxacarbocycanine; N,N'-dihexyl oxacarbocyanine; merocyanine, 4-(3'-pyrenyl)butyrate; d-3-aminodesoxy-equilenin; 12-(9'-anthroyl)stearate; 2-methylanthracene; 9-vinylanthracene; 2,2'-(vinylene-p-phenylene) bisbenzoxazole; p-bis[2-(4-methyl-5-phenyl oxazolyl)] benzene; 6-dimethylamino-1,2-benzophenzin; retinol; bis (3'-aminopyridinium)-1,10-decandiyl diiodide;

sulfonaphthylhydrazone of hellibrienin; chlorotetracycline; N-(7-dimethylamino-4-methyl-2-oxo-3-chromenyl)maleimide; N-[p-(2-benzimidazolyl)phenyl]maleimide; N-(4-fluoranthyl)maleimide; bis(homovanillic acid); resazarin; 4-chloro-7-nitro-2,1,3-benzooxadizole; merocyanine 540; resorufin; rose bengal and 2,4-diphenyl-3(2H)-furanone. In particular embodiments, the fluorescent detectable moiety is a fluorescein or rhodamine dye. More information about commercially available dyes for oligonucleotide conjugation can be found at the website accessed by typing "www" followed by ".synthegen.com" into the address bar of a typical internet browser. Any such dyes may potentially be used in accordance with the methods described herein.

Although the examples described herein use a fluorophore as the label, it will be apparent to those of ordinary skill that other observable label moieties may be used (instead of a fluorophore, or even in addition to a fluorophore). Such labels typically are well known in the art and include, for example, radiolabels (such as $^3H$, $^{125}I$, $^{35}S$, $^{14}C$ or $^{32}P$); chemiluminescent or bioluminescent labels (such as luminol, lophine, acridine salts and luciferins), which are electronically excited as the result of a chemical or biological reaction and subsequently emit light; spin labels (such as vanadium, copper, iron, manganese and nitroxide free radicals), which are detected by electron spin resonance (ESR) spectroscopy; dyes (such as quinoline dyes, triarylmethane dyes and acridine dyes), which absorb specific wavelengths of light.

In still other embodiments, the observable label moiety Obs may comprise small particles, e.g. magnetic particles; quantum dot nanoparticles; or colloidal gold (40-80 nm diameter), which scatters green light with high efficiency. The particles may be attached directly to the linking group Lnk or indirectly, e.g. via the interaction between antibiotin (e.g. conjugated to the particle) and a biotinylated linking group Lnk. The colloidal gold may be attached in a variety of ways, e.g. the linker moiety Lnk terminates in a thiol group (—SH), and the thiol group is directly bound to colloidal gold through a dative bond. See Mirkin et al. Nature 1996, 382, 607-609. The detection of the gold labeled compound may be enhanced through the use of a silver enhancement method. See Danscher et al. J. Histotech 1993, 16, 201-207.

In both structure (I) and structure (II), the observable label moiety Obs is attached to the linking group Lnk. The observable label moiety Obs may be attached to the linking group Lnk at any site of the observable label moiety Obs that is compatible with the intended use, e.g. with the labeling reaction in which the labeled nucleotide composition is used to label a polynucleotide. In other words, in the examples discussed below, the label moiety should not prevent the ligation reaction, e.g. by interfering with the enzyme having an RNA ligation activity. The observable label moiety Obs is typically attached to the sugar group via the linking group Lnk and the phosphate group at the 3' site of the sugar.

In particular embodiments, the linking group Lnk and the observable linker moiety Obs are selected to be compatible with an enzymatic labeling method wherein a labeled nucleotide composition described herein is enzymatically attached to a polynucleotide to provide a labeled polynucleotide. One such method is described below. In such embodiments, the labeled nucleotide composition is capable of being a substrate for an enzyme having an activity to attach the labeled nucleotide composition to a polynucleotide to provide a labeled polynucleotide.

Accordingly, in one embodiment of the present invention, a method of labeling RNA in a sample is provided. The method includes contacting the sample with an enzyme having an RNA ligation activity in the presence of a labeled nucleotide composition such as described herein (e.g. the compositions having structure (I) or structure (II)) under conditions sufficient to result in coupling of the labeled nucleotide composition to the RNA in the sample to provide labeled RNA. In certain embodiments, the conditions sufficient to result in coupling include a DMSO concentration in the range from about 20% to about 30%.

The sample may be any RNA sample, typically a sample containing RNA that has been isolated from a biological source, e.g. any plant, animal, yeast, bacterial, or viral source, or a non-biological source, e.g. chemically synthesized. The dimethylsulfoxide (DMSO) concentration is calculated as volume (e.g. in milliliters) of DMSO divided by total volume (e.g. in milliliters) of the solution containing the DMSO. This quantity is typically cast as a percentage by multiplying by 100%. For example, the DMSO concentration will be in a range of 20% to about 30%, calculated as the volume of DMSO in the solution resulting from contacting the sample with an enzyme having an RNA ligation activity in the presence of a labeled nucleotide composition, divided by the total volume of the solution, and then multiplying by 100%. The other components present in the resulting solution will typically be water, buffer components, salt, RNA, labeled nucleotide composition, and enzyme having an RNA ligation activity, although other components may also be present. In particular embodiments, the sample includes small RNAs, especially RNAs less than about 500 bases long, e.g. less than about 400 bases long, less than about 300 bases long, less than about 200 bases long, or less than about 100 bases long. In particular embodiments, the sample includes one or more short RNAs, such as e.g. short interfering RNAs (siRNAs), microRNAs (miRNA), tiny non-coding RNAs (tncRNA) and small modulatory RNA (smRNA). See Novina et al., Nature 430: 161-164 (2004). In particular embodiments, the sample includes isolated small RNAs, e.g. the sample results from an isolation protocol for small RNA such as one or more of those listed in this paragraph. In certain embodiments, the small RNA targets may include isolated miRNAs, such as those described in the literature and in the public website database accessible by typing "www" followed by ".sanger.ac.uk/cgi-bin/Rfam/mirna/browse.pl" into the address bar of a typical internet browser. In particular embodiments, the sample includes isolated small RNAs, e.g. the sample results from an isolation protocol for small RNA, especially RNAs less than about 500 bases long, e.g. less than about 400 bases long, less than about 300 bases long, less than about 200 bases long, less than about 100 bases long, or less than about 50 bases long.

The enzyme having an RNA ligation activity is typically any RNA ligase enzyme, although other enzymes capable of coupling the labeled nucleotide composition to the RNA may be used. In particular embodiments, the enzyme having an RNA ligation activity is capable of coupling a nucleotide having a 5' phosphate to an oligonucleotide (e.g. an RNA) having a 3' hydroxyl. Exemplary enzymes include T4 RNA ligase available from Amersham/Pharmacia company, ThermoPhage™ RNA ligase II (available from Prokaria LTD, Iceland), or other available RNA ligase enzymes known to be capable of coupling a nucleotide having a 5' phosphate to an oligonucleotide (e.g. and RNA) having a 3' hydroxyl. In certain embodiments, the enzyme may be selected from yeast poly A polymerase, *E. coli* poly A polymerase, or terminal transferase (each of which is available from Amersham/Pharmacia). The enzyme having an RNA ligation activity should be selected such that the enzyme is capable of performing the coupling when one (or both) of the nucleotide having a 5'phosphate and/or the oligonucleotide having a 3' hydroxyl includes a label. Selection of the enzyme having an RNA ligation activity will typically be based on availability of the enzyme and activity of the enzyme under the desired reaction conditions for the coupling (e.g. temperature, pH, ionic strength, source of RNA and/or labeled nucleotide composition, structural feature of RNA and/or labeled nucleotide composition, concentration of RNA and/or labeled nucleotide composition, presence of other materials (e.g. contaminants, salt, surfactant, other solvents) etc.)

The coupling reaction is conducted under conditions sufficient to result in coupling. The conditions of the coupling reaction will generally be selected with regard to the known (previously described) conditions for use of the particular enzyme chosen for use in the methods of the invention, with the specific modifications described herein. As already indicated, in particular embodiments, the DMSO of the reaction mixture for the coupling reaction will be in the range of 20% to 30%. Other experimental parameters may be selected based on known ranges for the experimental parameters or determined through routine experimentation based on, e.g. efficacy of the labeling reaction. Such other experimental parameters may include, e.g. temperature, pH, ionic strength, source of RNA and/or labeled nucleotide composition, structural feature of RNA and/or labeled nucleotide composition, concentration of RNA and/or labeled nucleotide composition, presence of other materials (e.g. contaminants, salt, surfactant, other solvents) etc.

An embodiment of a method in accordance with the present invention is illustrated in FIG. 1. In FIG. 1, the method 100 of labeling RNA includes adding 104 DMSO 106 to the sample (which includes the RNA 102). The labeled nucleotide composition 110 may then be added 108 to the resulting solution (containing the DMSO 106 and the RNA 102 from the sample). The labeled nucleotide composition 110 typically is a mononucleotide with a 3' fluorophore and 5' phosphate 110. The enzyme having an RNA ligation activity 114 is also added 112. In typical embodiments, the concentrations of the solutions and the volumes added are planned to provide that the resulting solution has the desired concentration of DMSO (e.g. in the range of about 20% to about 30%, more typically in the range of about 22% to about 28%, even more typically in the range of about 24% to about 26%). The resulting solution is then allowed to react 116 under conditions and for a time sufficient for the coupling of the labeled nucleotide composition to the RNA to occur, thereby providing the labeled RNA 118. Typical conditions 120 of overnight incubation at 16° C. are shown for the embodiment of FIG. 1, although these conditions may vary depending on the particular enzyme used and the RNA and labeled nucleotide composition provided. In the illustrated embodiment, the label is a fluorophore 111, but other labels may be used as long as the coupling of the labeled nucleotide composition to the RNA may still occur. Selection and optimization of the conditions is within routine experimentation for one of ordinary skill in the art given the disclosure herein.

In the embodiment illustrated in FIG. 1, the labeled nucleotide composition denominated 110 is shown as a mononucleotide attached to a fluorophore. In certain embodiments, the labeled nucleotide composition may include more than one nucleotide subunit linked together, e.g. the phosphate group P1 of structure (I) may form a phosphodiester linkage between the Nus group and a second nucleotide subunit. In particular embodiments, up to 2, 3, 4, 5, or more nucleotide subunits, up to about 10, 20, 30 or more nucleotide subunits, may be linked to the labeled nucleotide substrate, such that the labeled nucleotide substrate is part of an oligonucleotide. In such embodiments, the observable label moiety is attached to the oligonucleotide via the 3' terminal carbon of the oligonucleotide via the phosphate group bound at the 3' terminal carbon of the oligonucleotide, and the oligonucleotide has a 5' phosphate group.

In particular embodiments, the enzyme having an RNA ligation activity catalyzes a coupling reaction between a donor molecule having a 5'-phosphate and an acceptor molecule having a 3'-hydroxyl, as shown in the reaction:

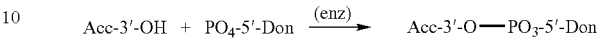

Where: Acc-3'-OH is the acceptor molecule having a 3'-hydroxyl;
PO$_4$-5'-Don is the donor molecule having a 5'-phosphate;
Acc-3'-O—PO$_3$-5'-Don is the product having the coupled donor and acceptor moieties (e.g. the labeled RNA); and
(enz) is the enzyme having an RNA ligation activity.

In embodiments such as that illustrated in FIG. 1, the acceptor molecule is the RNA 102 and the donor molecule is the labeled nucleotide composition 110. The resulting product 118 has the labeled nucleotide composition moiety downstream from the RNA, i.e. the product is a downstream labeled RNA.

It should be noted that the general utility of the method is not limited to the particular sequence of steps shown in the figures. Other sequences of steps leading to essentially similar results are intended to be included in the invention. For example, in certain embodiments, the labeled nucleotide composition may be dissolved in a solution that includes the DMSO, and the resulting solution mixed with the sample prior to contacting with the enzyme having an RNA ligase activity. Thus, in particular embodiments, the invention includes any process which results in contacting the sample with the enzyme having an RNA ligation activity in the presence of the labeled nucleotide composition under conditions which include a DMSO concentration in the range from about 20% to about 30%.

With reference to FIG. 1, in certain embodiments, after the DMSO 106 is added 104 and before the enzyme having an RNA ligation activity 114 is added 112, the method 100 includes heating the solution containing the DMSO 106 and the RNA 102 from the sample. In this optional heating step, the RNA is typically heated to a temperature of at least about 80° C. (e.g. at least about 85° C., at least about 90° C., at least about 95° C.; and up to about 105° C. or 110° C.) under conditions that include a DMSO concentration of at least about 40% DMSO (typically up to about 60% DMSO, although in some embodiments the DMSO concentration may be up to 70% DMSO, up to 80% DMSO, or even more). This optional heating is maintained for at least 10 seconds, typically at least about 20 seconds, at least about 30 seconds, at least about 1 minute, at least about 2 minutes, and up to about 15 minutes, or more. In particular embodiments, reaction solutions of up to about 50 microliters are heated for about 30 to about 60 seconds per 5-10 microliters of reaction solution. After the heating, the RNA is typically quickly cooled (e.g. to less than about 40° C., more typically less than about 20° C., or in some embodiments less than about 5° C.) before adding the enzyme having an RNA ligation activity.

It should be noted that, in particular embodiments, the RNA in the sample is isolated via a process that results in the RNA in the sample having a 5'-phosphate. For embodiments such as that pictured in FIG. 1, in which the RNA in the sample does not have a 5'-phosphate, a preparatory treatment of subjecting the RNA in the sample to a dephosphorylation reaction is conducted prior to labeling the RNA in the sample by the ligation method illustrated in FIG. 1. Such dephosphorylation reactions are well known in the art, for example, treating the RNA sample with an enzyme having a 5'-phosphatase activity, e.g. calf intestine alkaline phosphatase, shrimp alkaline phosphatase, or *E. coli* alkaline phosphatase, or any other method of dephosphorylating the RNA known in the art. Thus, in certain embodiments, the method of labeling RNA in a sample includes, prior to contacting the sample with the enzyme having an RNA ligation activity, contacting the sample with an enzyme having a 5'-phosphatase activity to remove 5'-phosphate groups from the RNA in the sample.

In certain embodiments, methods of performing an array analysis of an RNA sample are provided. In certain embodiments, the invention provides a method of performing an array analysis wherein the method includes labeling the RNA in the sample to provide labeled RNA using a labeling method in accordance with the methods described herein. The labeled RNA is then contacted with an array under conditions sufficient to provide for specific binding of labeled RNA to the array. The array typically is then interrogated to provide data on binding of the labeled RNA to the array.

Standard hybridization techniques (using stringent hybridization conditions) are used to hybridize a labeled sample to a nucleic acid array. Suitable methods are described in references describing CGH techniques (Kallioniemi et al., Science 258:818-821 (1992) and WO 93/18186). Several guides to general techniques are available, e.g., Tijssen, Hybridization with Nucleic Acid Probes, Parts I and II (Elsevier, Amsterdam 1993). For descriptions of techniques suitable for in situ hybridizations, see Gall et al. Meth. Enzymol., 21:470-480 (1981); and Angerer et al. in Genetic Engineering: Principles and Methods (Setlow and Hollaender, Eds.) Vol 7, pgs 43-65 (Plenum Press, New York 1985). See also U.S. Pat. Nos. 6,335,167; 6,197,501; 5,830,645; and 5,665,549; the disclosures of which are herein incorporated by reference. Hybridizing the sample to the array is typically performed under stringent hybridization conditions, as described herein and as known in the art. Selection of appropriate conditions, including temperature, salt concentration, polynucleotide concentration, time(duration) of hybridization, stringency of washing conditions, and the like will depend on experimental design, including source of sample, identity of capture agents, degree of complementarity expected, etc., and are within routine experimentation for those of ordinary skill in the art to which the invention applies.

Following hybridization, the array-surface bound polynucleotides are typically washed to remove unbound and not tightly bound labeled nucleic acids. Washing may be performed using any convenient washing protocol, where the washing conditions are typically stringent, as described above.

Following hybridization and washing, as described above, the hybridization of the labeled target nucleic acids to the capture agents is then detected using standard techniques of reading the array, i.e. the array is interrogated. Reading the resultant hybridized array may be accomplished by illuminating the array and reading the location and intensity of resulting fluorescence at each feature of the array to detect any binding complexes on the surface of the array. For example, a scanner may be used for this purpose, which is similar to the AGILENT MICROARRAY SCANNER available from Agilent Technologies, Palo Alto, Calif. Other suitable devices and methods are described in U.S. patent applications: Ser. No. 09/846,125 "Reading Multi-Featured Arrays" by Dorsel et al.; and U.S. Pat. No. 6,406,849. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). In the case of indirect labeling, subsequent treatment of the array with the appropriate reagents may be employed to enable reading of the array. Some methods of detection, such as surface plasmon resonance, do not require any labeling of nucleic acids, and are suitable for some embodiments.

Results from the reading or evaluating may be raw results (such as fluorescence intensity readings for each feature in one or more color channels) or may be processed results (such as those obtained by subtracting a background measurement, or by rejecting a reading for a feature which is below a predetermined threshold, normalizing the results, and/or forming conclusions based on the pattern read from the array (such as whether or not a particular target sequence may have been present in the sample, or whether or not a pattern indicates a particular condition of an organism from which the sample came).

In certain embodiments, results from interrogating the array are used to assess the level of binding of the population of labeled nucleic acids to capture agents on the array. The term "level of binding" means any assessment of binding (e.g. a quantitative or qualitative, relative or absolute assessment) usually done, as is known in the art, by detecting signal (i.e., pixel brightness) from a label associated with the sample nucleic acids, e.g. the digested sample is labeled. The level of binding of labeled nucleic acid to capture agent is typically obtained by measuring the surface density of the bound label (or of a signal resulting from the label).

In certain embodiments, a surface-bound polynucleotide may be assessed by evaluating its binding to two populations of nucleic acids that are distinguishably labeled. In these embodiments, for a single surface-bound polynucleotide of interest, the results obtained from hybridization with a first population of labeled nucleic acids may be compared to results obtained from hybridization with the second population of nucleic acids, usually after normalization of the data. The results may be expressed using any convenient means, e.g., as a number or numerical ratio, etc.

EXAMPLES

The practice of the present invention will employ, unless otherwise indicated, conventional techniques of synthetic organic chemistry, biochemistry, molecular biology, and the like, which are within the skill of the art. Such techniques are explained fully in the literature. Unless otherwise defined herein, all technical and scientific terms used herein have the same meaning as commonly understood by one of ordinary skill in the art to which the invention belongs.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. Standard temperature and pressure are defined as 20° C. and 1 atmosphere.

Methods:

RNA ligation was assessed with synthetic RNA oligonucleotides (21-23 nucleotides, Dharmacon) in reaction solutions containing 0, 15, 20, 25, and 30% DMSO. The reactions containing 25% DMSO were assayed with and without the pre-heating step. Stock solutions of 20 μM RNA oligonucleotides were stored in 1×TE (10 mM Tris-HCl, pH 7.5, 1 mM EDTA). Initial mixtures of RNA, DMSO and water were first assembled. For pre-heated samples, the heated mixture contained 40-70% DMSO and were heated using a 104° C. heating block for 1.5-2 minutes. The heated samples were immediately set on ice for >5 minutes prior to final assembly. The final reaction contains 1× Amersham Pharmacia RNA ligase buffer (50 mM Tris-HCl, pH 7.5, 10 mM MgCl$_2$, 10 mM DTT, 1 mM ATP, 60 ng/μL BSA) 1 unit/μL T4 RNA ligase, 1100M, 5'-phosphate-cytidyl-phosphate-Cy5-3' (pCpCy5) or 5'-phosphate-cytidyl-phosphate-Cy3-3'(pCpCy3) (Dharmacon) and 2-4 μM RNA oligonucleotides. The reactions were incubated at 16° C. overnight. RNA ligase was inactivated by heating the reaction solutions using a 104° C. heating block for 1.5-2 minutes, followed by immediately setting on ice for >5 minutes.

The labeling efficiency was determined by 5'-phosphorylation of RNA ligation reaction aliquots with radioactive $P^{32}$-gamma-ATP. The resulting mixture was desalted with Micro Bio-Spin™ (BioRad) desalting columns. The desalted mixture was loaded onto denaturing polyacrylamide gel. Since the ligation products contain an extra nucleotide and fluorophore, they have a lower electrophoretic migration rate than the unligated precursors. $P^{32}$-labeled RNA bands are visualized and quantified with phosphorimager (Molecular Dynamics). The ligation efficiency was determined by the ratio of ligated vs. unligated $P^{32}$-labeled RNA bands. Thus, ligation efficiency may be expressed as the mol % of initial RNA that winds up having an attached label moiety.

Description of Synthesis:

The general approach to the synthesis of pCp-Label is illustrated below.

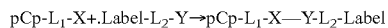

pCp-L$_1$-X+.Label-L$_2$-Y→pCp-L$_1$-X—Y-L$_2$-Label in which L$_1$ is a linker and X is a reactive functionality, and L$_2$ is a linker and Y is an activated or activatable functionality, and Label is an observable label moiety as described herein. In the reaction product, functionalities -L$_1$-X—Y-L$_2$- provide the linking group Lnk as described herein.

For example, L$_1$ can be a six carbon chain, X can be an amino functionality. L$_2$ can be a five carbon chain terminated by a carboxylic acid. In the presence of an activating agent such as a carbodiimide reagent, L$_1$ and L$_2$ will be coupled through an amide bond. Alternatively, a five carbon L$_2$ can be terminated by the activated N-hydroxysuccinimide (NHS) ester Y. In this case no activating agent is necessary, and formation of the amide bond will form when the two reagents are mixed together under conditions well known in the art.

The observable label moiety may be any moiety that will enable or enhance detection of the desired compound. Exemplary labels include the fluorescent dyes cy5 and cy3.

The synthesis of a suitable labeled pCp derivative can be performed in a number of ways. One such scheme is outlined in FIG. 2, FIG. 3, and FIG. 4. In order to create a pCp molecule that can be further functionalized with a fluorescent label, a resin containing a C-6 amino linker, compound 1 (Glen Research), can be used. Using standard solid phase RNA synthesis chemistry, compound 1 can be further elaborated as follows. Treatment of compound 1 with acid such as dichloroacetic acid to remove the trityl blocking group gives compound 2. Coupling of compound 2 with phosphoramidite 3 in the presence of an activator such as 5-Ethylthio-1H-Tetrazole gives phosphite ester 4. Depending on the exact details of the RNA synthesis, a variety of blocking and protecting groups can be used. For example, in FIG. 2, the exocyclic amine protecting group can be acetyl, the 2'-hydroxyl protecting group can be tert-butyldimethylsilyl, the phosphite ester group R can be beta-cyanoethyl, and the 5'-hydroxyl blocking group can be dimethoxytrityl. After the oxidation step (typically with a solution of iodine in THF/pyridine/water), phosphate 5 is obtained.

Continuing on to FIG. 3, removal of the 5'-hydroxyl blocking group with dichloroacetic acid gives the compound 6. Coupling with a chemical phosphorylating reagent such as 2-[2-(4,4'-Dimethoxytrityloxy)ethylsulfonyl]ethyl-(2-cyanoethyl)-(N,N-diisopropyl)-phosphoramidite (available from Glen Research), followed by oxidation, gives the blocked and protected diphosphate compound 7, where R' is the cleavable part of the chemical phosphorylating agent. It should be noted, that although not shown, as is known in the art, a capping step can be performed if desired after any or each coupling step in the synthesis.

The resin bound compound 7 is treated under basic conditions such as aqueous ammonia in order to cleave the resin linker and remove all the protecting groups except the one on the 2'-hydroxyl, giving rise to the amine containing compound 8. Removal of the 2'-hydroxyl protecting group is performed using a fluoride containing reagent such as tetrabutylammonium fluoride solution in THF, giving rise to pCp-hexylamine 9

Continuing on to FIG. 4, the pCp-hexylamine 9 can be coupled to an appropriate label. The cy5-linker-NHS ester compound 10 is coupled to the hexylamine 9, typically under slightly basic conditions. This gives rise to the desired pCp-cy5 compound 11.

FIG. 5 shows a mass spectrogram of a pCp-cy5 compound.

Description of Labeling RNA:

In the experiments described here, T4 RNA ligase is used to label synthetic RNA oligonucleotides with 5'-phosphate-cytidyl-phosphate-Cy5-3' (pCpCy5) or 5'-phosphate-cytidyl-phosphate-Cy3-3' (pCpCy3). The reaction conditions described here have been observed to result in ligation efficiencies of about 60% or more, e.g. about 70% or more, or 80% or more, up to about 95% or more, e.g. up to about 99% with minimal sequence discrimination. This was accomplished by reacting at 25% DMSO, 16° C. overnight, with donor to acceptor ratio of >12.5:1. The reaction buffer contains 50 mM Tris-HCl, pH 7.5, 10 mM MgCl2, 10 mM DTT, 1 mM ATP, 60 μg/mL BSA, and 25% DMSO. Typical reactions are 10 μL with 2 μM RNA, 100 μM pCpCy5 or pCpCy3, and 4 units T4 RNA ligase (Amersham/Pharmacia). Reaction efficiency seemed unaffected by increasing the RNA concentration to 8 μM or decreasing enzyme to 2 units.

The labeling efficiency was determined by first performing the ligation reaction. An aliquot of the ligation mixture was then labeled on the 5' end with radioactive $P^{32}$-γ-ATP and T4 Polynucleotide Kinase. The control sample, which did not undergo ligation reaction, and final reaction mixture was denatured with formamide and assessed with denaturing polyacrylamide gel electrophoresis (1× or 0.5×TBE, 50% urea, 15-20% polyacrylamide with 19:1 acrylamide to bisacrylamide ratio, at about 50° C.). The resulting gel was scanned with Molecular Dynamics Storm Phosphorimager for pCpCy5-labeled RNA. The ligation product was clearly visible as a red fluorescent miRNA. The gel was then exposed to phosphor screen to determine the pCpCy5-labeling efficiency. Since the addition of pCpCy5 increases the acceptor miRNA by 1 nucleotide and a fluorophore, the mobility of the Cy5-labeled strand was lower than the unreacted strand. They appear as distinct bands when scanned in the phosphor mode on the phosphoimager; this was further verified by the relative mobility between the ligase reacted samples and unreacted controls (both the ligase reacted samples and the unreacted controls were labeled with $P^{32}$-γ-ATP). Thus the relative level of radioactivity between the Cy-labeled and unlabeled bands reveals the ligation efficiency. The reaction efficiency of pCpCy3 was determined similarly except the Cy3 labeled strand was undetectable by the fluorescent mode of the phosphorimager. The product and reactant miRNA bands of the Cy3 reaction were defined by the mobility of Cy5 reactions in polyacrylamide gel electrophoreseis and phosphorimager analysis.

Ligation efficiency under different reaction conditions was extensively tested with pCpCy5 and 4 separate synthetic oligonucleotides (SEQ ID NOs:1-4), each of which contains the same sequence as *drosophila* miRNA (as indicated):

TABLE 1

Test Sample miRNAs

| SEQ ID NO: | Name | Sequence | 3' Terminal NT | #NT |
|---|---|---|---|---|
| 1 | dme-miR-3 | UCACUGGGCAAAGUGUGUCUCA | A | 22 |
| 2 | dme-let-7 | UGAGGUAGUAGGUUGUAUAGU | U | 21 |
| 3 | dme-miR-14 | UCAGUCUUUUUCUCUCUCCUA | A | 21 |
| 4 | dme-miR-31a | UGGCAAGAUGUCGGCAUAGCUGA | A | 23 |

These miRNAs were labeled with 80-99% efficiency when the reaction mixture contained 95% (molar ratio) competitors composing of other miRNAs and longer single stranded RNAs (100-500 nts). Thus it is reasonable to expect high labeling efficiency in heterogeneous biological RNA mixtures.

After optimization of labeling efficiencies of these RNAs with Cy5, the labeling reaction was expanded to include the following sequences (SEQ ID NOs:6-10) with pCpCy5 and pCpCy3 in separate studies. These additional strands address any bias that may result from 3' terminal nucleotide, potential secondary structures and nucleotide content of the miRNA.

example, in an array hybridization experiment wherein an array is contacted with a labeled RNA sample, it is possible to ascertain the total quantity of fluorophores in a given area of the array by interrogating (or scanning) the array; given the labeling efficiency of the labeled RNA sample (determined as disclosed herein), the quantity of RNA hybridized to the given area of the array may be determined.

Given that the approximate labeling efficiency may be determined (as described herein), in particular embodiments the present invention thus provides quantitative methods of performing array hybridization experiments. It is expected that this will provide a more sensitive assay system for the detection of variations of miRNA, such as found in developmental stages, tissue samples, disease states, as well as any individual and/or abnormal variations. Moreover, if more viral miRNAs are identified, this can become a novel diagnostic tool for active as well as latent viral infections Determination of Labeling Efficiency of miRNAs in Complex Samples:

RNA ligase is used to label a complex RNA mixture, such as the total RNA or isolated mixtures of small RNAs from biological samples. The labeled mixtures are run on denaturing polyacrylamide gel and Northern blots are performed of individual miRNAs with radioactive probes. The RNAs labeled by RNA ligase will have a lower mobility relative to its unlabeled counterpart. Thus each target sequence will run as a doublet when probed by Northern blot. The ratio of RNA species in these doublets reflects the molar ratio of the RNA ligase labeled vs. unlabeled RNA species.

TABLE 2

Additional Test Sample miRNAs

| SEQ ID NO: | Name | Sequence | 3' Terminal NT | #NT |
|---|---|---|---|---|
| 5 | dme-miR-2b | UAUCACAGCCAGCUUUGAGGAGC | C | 23 |
| 6 | dme-miR-6 | UAUCACAGUGGCUGUUCUUUUU | U | 22 |
| 7 | dme-miR-184* | CCUUAUCAUUCUCUCGCCCCG | G | 21 |
| 8 | dme-miR-285 | UAGCACCAUUCGAAAUCAGUGC | C | 22 |
| 9 | dme-miR-308 | AAUCACAGGAUUAUACUGUGAG | G | 22 |
| 10 | dme-miR-316 | UGUCUUUUUCCGCUUACUGGCG | G | 22 |

Potentially, the RNA ligase method can be used for dyes other than Cy5 and Cy3, but the efficiency may differ from the ones presented here. Moreover, it is possible to determine the labeling efficiencies of each individual miRNA of a given set and perform highly quantitative microarray experiments by correlating fluorophore counts with number of molecule. For Microarray Hybridization:

The synthetic miRNA set forth above were either labeled with Cy5 or Cy3 and hybridized onto microarrays as follows:

Labeled miRNA were desalted with BioRad Micro Bio-Spin™ 6 (as directed by BioRad instructions) to remove free fluorescent tags. The desalted miRNA was added to solution containing water and carrier (25-mer DNA with random sequence). The solution was heated for approximately 1 minute per 10 ul solution at 100° C. and immediately placed on ice. After cooling, 2× Agilent Hyb Buffer (1225 mM LiCl, 300 mM Li-MES, pH 6.1, 12 mM EDTA, 3.0% (w/v) lithium dodecyl sulfate, 2.0% (w/v) Triton X-100) was added to the mixture and the viscous liquid was mixed carefully. The final solution contained 1× Hyb Buffer and 0.1 µg/µl random 25-mer. The concentration of miRNA was varied for different experiments.

Hybridization was performed with SureHyb hybridization chamber (Agilent Part Number: G2534A) and place on rotisserie of hybridization oven overnight. The hybridization temperature was tested at 50° C. and 60° C.

After hybridization was completed, the Sure-Hyb chamber complex was removed from the oven and immediately disassembled in Wash Buffer 1 (6×SSC, 0.005% Triton X-102) at room temperature. The microarray was transferred to a fresh wash chamber containing Wash Buffer 1 and washed by stirring for 10 minutes at room temperature. The microarray was then washed in Wash Buffer 2 (0.1×SSC, 0.005% Triton X-102) by stirring at room temperature for 5 minutes. The microarray was slowly lifted out of the wash chamber after washing and dried with nitrogen as needed. The microarrays were scanned with Agilent Scanner (Agilent Product Number: G2565BA). The scanned data was extracted with Agilent Feature Extraction Software (Agilent Product Number; G2567AA) and the green and red background-subtracted signals were evaluated for hybridization efficiency and specificity. Data was further analyzed using Spotfire software and Microsoft Excel.

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties, provided that, if there is a conflict in definitions, the definitions provided herein shall control.

What is claimed is:

1. A composition having the structure (I):

P1-Nus-P2-Lnk-Obs    (I)

or a salt, conjugate base, tautomer, or ionized form thereof, wherein:
  P1 is a phosphate group,
  Nus is a nucleoside moiety comprising a sugar group bound to a purine or pyrimidine base;
  P2 is a phosphate group;
  Lnk is a linking group; wherein Lnk has the structure —(CH$_2$)$_m$-Lkg-(CH$_2$)$_n$— wherein m and n are integers independently selected from the range of 1 to about 12, and Lkg is a linkage selected from ether-, thio-, amino-, oxo-, ester-, and amido-; and
  Obs is an observable label moiety.

2. The composition of claim 1, wherein the sugar group has a 5' site, a 3' site, and a 1' site, P1 is attached to the sugar group at the 5' site, P2 is attached to the sugar group at the 3' site, and the purine or pyrimidine base is attached to the sugar group at the 1' site.

3. The composition of claim 1, wherein the sugar group is ribose and the purine or pyrimidine base is selected from adenine (A), cytosine (C), guanine (G), or uracil (U).

4. The composition of claim 1, wherein the purine or pyrimidine base is selected from 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine, or 2,6-diaminopurine.

5. The composition of claim 1, wherein the observable label moiety is selected from a chromogenic moiety, a fluorophore, a mass label, a spin label, or a radiolabel.

6. The composition of claim 1, wherein the observable label moiety is a fluorophore selected from the group consisting Cy3, Cy5, or an Alexa dye.

7. A composition having the structure (II):

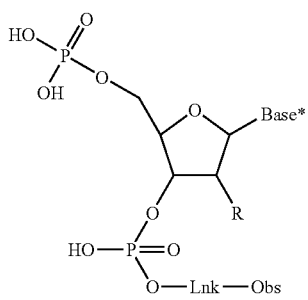

(II)

or a salt, conjugate base, tautomer, or ionized form thereof, wherein:

Base* is a purine or pyrimidine base;

R is H, OH, or a hydroxyl protecting group;

Lnk is a linking group, wherein Lnk has the structure

—$(CH_2)_m$-Lkg-$(CH_2)_n$— wherein m and n are integers independently selected from the range of 1 to about 12, and wherein Lkg is a linkage selected from ether-, thio-, amino-, oxo-, ester-, and amido-; and Obs is an observable label moiety.

8. The composition of claim 7, wherein the sugar group is ribose and the purine or pyrimidine base is selected from adenine (A), cytosine (C), guanine (G), or uracil (U).

9. The composition of claim 7, wherein the purine or pyrimidine base is selected from 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine, or 2,6-diaminopurine.

10. The composition of claim 7, wherein the observable label moiety is selected from a chromogenic moiety, a fluorophore, a mass label, a spin label, or a radiolabel.

11. The composition of claim 7, wherein the observable label moiety is a fluorophore selected from the group consisting Cy3, Cy5, or an Alexa dye.

* * * * *

```
                        SEQUENCE LISTING

<160> NUMBER OF SEQ ID NOS: 10

<210> SEQ ID NO 1
<211> LENGTH: 22
<212> TYPE: RNA
<213> ORGANISM: Drosophila melanogaster

<400> SEQUENCE: 1
ucacugggca agugugucu ca                                          22

<210> SEQ ID NO 2
<211> LENGTH: 21
<212> TYPE: RNA
<213> ORGANISM: Drosophila melanogaster

<400> SEQUENCE: 2
ugagguagua gguuguauag u                                          21

<210> SEQ ID NO 3
<211> LENGTH: 21
<212> TYPE: RNA
<213> ORGANISM: Drosophila melanogaster

<400> SEQUENCE: 3
ucagucuuuu ucucucuccu a                                          21

<210> SEQ ID NO 4
<211> LENGTH: 23
<212> TYPE: RNA
<213> ORGANISM: Drosophila melanogaster

<400> SEQUENCE: 4
uggcaagaug ucggcauagc uga                                        23

<210> SEQ ID NO 5
<211> LENGTH: 23
<212> TYPE: RNA
<213> ORGANISM: Drosophila melanogaster

<400> SEQUENCE: 5
```

```
uaucacagcc agcuuugagg agc                                          23

<210> SEQ ID NO 6
<211> LENGTH: 22
<212> TYPE: RNA
<213> ORGANISM: Drosophila melanogaster

<400> SEQUENCE: 6
uaucacagug gcuguucuuu uu                                           22

<210> SEQ ID NO 7
<211> LENGTH: 21
<212> TYPE: RNA
<213> ORGANISM: Drosophila melanogaster

<400> SEQUENCE: 7
ccuuaucauu cucucgcccc g                                            21

<210> SEQ ID NO 8
<211> LENGTH: 22
<212> TYPE: RNA
<213> ORGANISM: Drosophila melanogaster

<400> SEQUENCE: 8
uagcaccauu cgaaaucagu gc                                           22

<210> SEQ ID NO 9
<211> LENGTH: 22
<212> TYPE: RNA
<213> ORGANISM: Drosophila melanogaster

<400> SEQUENCE: 9
aaucacagga uuauacugug ag                                           22

<210> SEQ ID NO 10
<211> LENGTH: 22
<212> TYPE: RNA
<213> ORGANISM: Drosophila melanogaster

<400> SEQUENCE: 10
ugucuuuuuc cgcuuacugg cg                                           22
```